United States Patent [19]

Steer et al.

[11] Patent Number: 4,462,510
[45] Date of Patent: Jul. 31, 1984

[54] TAP FOR DRAINAGE BAG

[75] Inventors: Peter L. Steer; John V. Edwards, both of East Grinstead, England

[73] Assignee: Kingsdown Medical Consultants Limited, London, England

[21] Appl. No.: 391,658

[22] Filed: Jun. 24, 1982

[30] Foreign Application Priority Data

Jun. 30, 1981 [GB] United Kingdom ............ 8138193

[51] Int. Cl.³ ............................................. B67D 3/00
[52] U.S. Cl. .................................... 222/48; 604/248; 604/323; 251/310; 137/218; 222/484; 222/554; 222/553; 222/189
[58] Field of Search ............... 604/32, 248, 323, 335, 604/333, 129; 251/309, 310; 137/217, 218; 222/48, 189, 481, 481.5, 484, 548, 554, 501, 469, 520, 553

[56] References Cited

U.S. PATENT DOCUMENTS

| | | | |
|---|---|---|---|
| 532,990 | 1/1895 | Rau | 222/554 |
| 3,057,350 | 10/1962 | Cowley | 604/248 |
| 3,173,579 | 3/1965 | Curie et al. | |
| 3,223,117 | 12/1965 | Curie et al. | |
| 3,430,824 | 3/1969 | Conners et al. | |
| 3,484,027 | 12/1969 | Micallef | 222/554 |
| 3,598,150 | 8/1971 | Nolan | |
| 3,642,172 | 2/1972 | Malpas | 222/554 |
| 3,823,716 | 7/1974 | Hale | |
| 4,003,403 | 1/1977 | Nehring | 251/309 |

Primary Examiner—H. Grant Skaggs
Attorney, Agent, or Firm—Lawrence S. Levinson; Sanford J. Asman

[57] ABSTRACT

A tap for a drainage bag includes a rotatable valve which is adapted to be readily taken apart for cleaning. The valve includes a body, having a cylindrical recess formed therein, and a cylindrical valve member which fits into the cylindrical recess in the body. The body is secured to a flat flange of plastic, which flange is typically welded, or adhesively fixed, in a face-to-face manner to a wall of the bag. The construction method used to make the tap is particularly well suited to rapid mass-production methods of manufacture.

12 Claims, 7 Drawing Figures

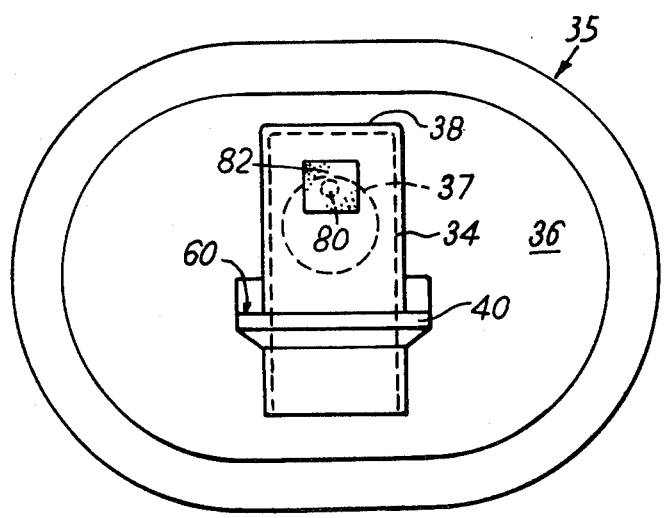
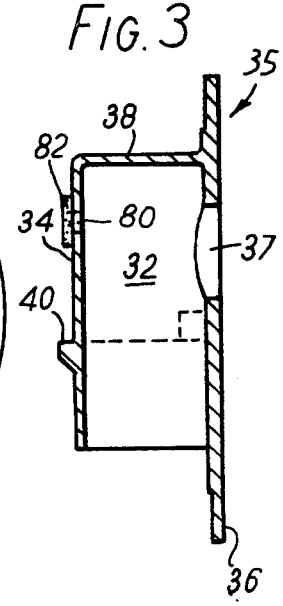
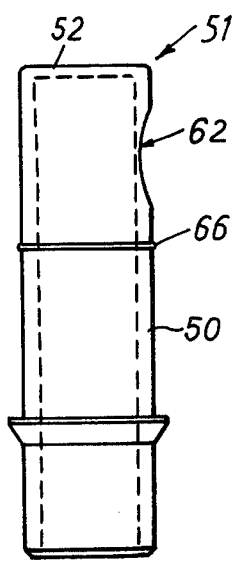
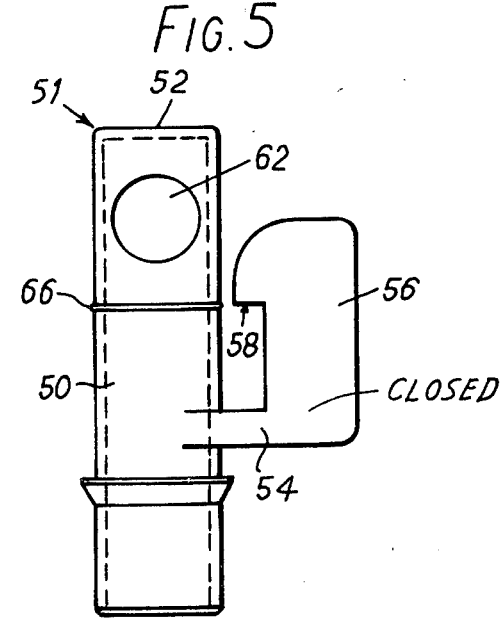

TAP FOR DRAINAGE BAG

BACKGROUND OF THE INVENTION

The present invention relates to a tap for a drainage bag.

Various types of taps for drainage bags have heretofore been known. One design, known as the CARMO tap, has a tubular valve member within a tubular housing. The valve member is moved axially to alternately expose or close off the taps by alignment or non-alignment, respectively, of corresponding ports in the housing and the valve member. The CARMO tap is inexpensive, but it is not easy to fit to a bag in a rapid mass-production process, and it is difficult for a user (particularly an aged or infirm user) to manipulate. Similar tap designs are shown in British Patent Specification Nos. 1 016 018, and 1 198 382.

Other known forms of tap are shown in British Patent Specification Nos. 1 308 519, and 1 310 581.

SUMMARY OF THE INVENTION

The present invention aims to provide a tap which can be readily fixed in a face-to-face manner to a wall of a plastic drainage bag. Also, the tap of the present invention is easy to operate.

According to the present invention, a tap for a drainage bag has a body with a valve member therein. The valve member is held within the body by engagement of a deformable handle positioned on the member. The deformable handle engages with a rib located on the exterior of the body.

According to the preferred embodiment of the invention, there is provided a tap for a drainage bag which includes two interengageable parts. The first part is a body having a substantially cylindrical recess. The first part includes a flange, whereby the body may be secured to a wall of the bag. The second part is a valve member which is insertable and rotatable in the cylindrical recess of the body. The valve member is in the form of a substantially hollow tube having a port. At one rotational position of the valve member relative to the body, the port in the valve member registers with a port in the body, thereby opening the valve. The valve member has a handle portion which extends substantially radially therefrom. The handle has a deformable detent engageable with a rib on the body. When the detent on the handle engages the rib on the body, as in normal use, the valve member is held within the body. Yet the valve member is not prevented from rotating relative to the body.

According to a preferred feature of the invention, the handle is in the form of a flat blade secured to or integral with an arm projecting radially outwardly from the valve member. The handle may have one side marked or coded (e.g., by color or other indicia) to indicate that the valve is "closed". The other side is marked or coded to indicate that the valve is "open". The body is preferably integral with or secured to a flat flange of plastic material. Such a flange is readily heat-welded, or adhesively fixed, in a face-to-face manner, to a wall of the bag, and such fixing is particularly well suited to rapid mass-production methods of manufacture.

The body and the valve member can be readily separated when it is desired to clean or sterlize the tap.

BRIEF DESCRIPTION OF THE DRAWING

FIG. 2 is a front view of the body part of the tap shown in FIG. 1;

FIG. 3 is a side view of the body part shown in FIG. 2;

FIG. 4 is a side view of a valve member of the tap shown in FIG. 1;

FIG. 5 is a part view of the valve member shown in FIG. 4;

DETAILED DESCRIPTION OF THE PREFERRED EMBODIMENT

Figure 1:
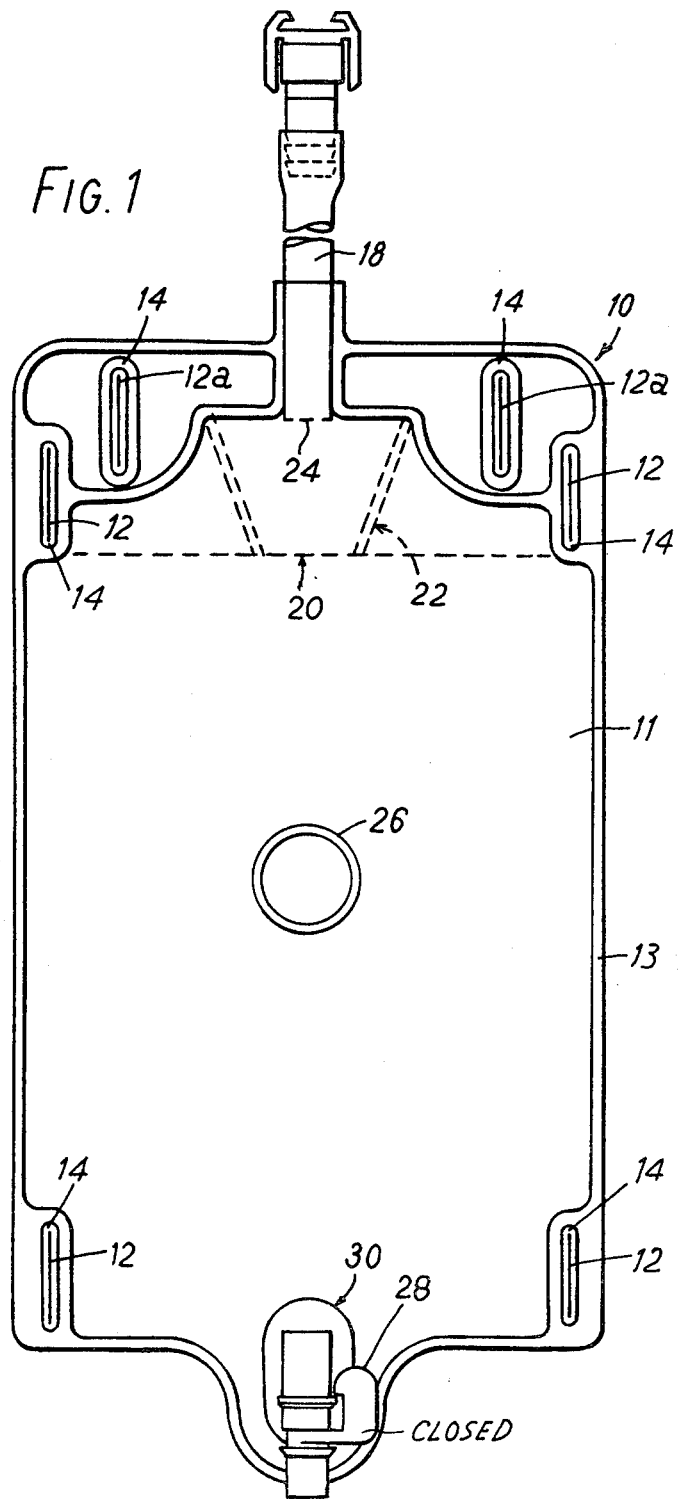
FIG. 1 is a front view of a drainage bag including an example of a tap according to the invention.

The drainage bag 10 of the present invention is illustrated in FIG. 1. The bag 10 is made from two sheets of plastic which are joined together around their edges, preferably by a weld seam 13 of the "double tramline" type. A number of slits 12 are provided through the superposed pair of plastic sheets 11 which constitute the walls of the bag 10. The slits 12 are preferably surrounded by strengthening beads 14. The slits 12 are provided in order that they be able to receive straps or tapes (not shown) for fastening the bag 10 to a user's leg. There are also slits 12a to facilitate hanging the bag 10 up, if desired. The bag 10 includes an integral inlet tube 18. The upper region of the bag 10 includes a non-return or anti-reflux valve 20. The anti-reflux valve 20 is preferably made of a single piece of plastic, which in combination with one of the walls 11 of the bag 10, to which it is welded, as shown at 22, defines a liquid entry space immediately downstream of the outlet 24 of the tube 18.

In the preferred embodiment of the invention, the center portion of the walls 11 of the bag 10 are preferably welded together using a closed-loop weld 26 which is typically of circular configuration. The weld 26 prevents undue "pouching" or "bulging" of the bag 10 as the bag 10 fills with liquid.

While the bag 10 is generally rectangular, its lower region has a downwardly extending extension 28 to receive the tap 30 which is welded or otherwise secured thereto.

The tap 30 is comprised of a body 35, shown in FIGS. 2 and 3, and a valve member 51, shown in FIGS. 4 and 5. The valve body 35 is preferably made of platic, and it is typically injection molded. The valve body 35 includes a generally cylindrical recess 32, and the substantially cylindrical wall 34 of the recess 32 is attached to, or integral with, a flat flange 36. The recess 32 is closed by a top wall 38. An external rib 40 is integral with the wall 34 and merges into the flange 36. A liquid exit port 37 extends through the flange 36 and opens into the recess 32. When the valve body 35 is secured to the wall 11 of the bag 10, the liquid exit port 37 is aligned with a hole or aperture (not shown) which is pre-punched in the wall 11 of the bag 10. Thus, a liquid communication path extends from the interior of the bag 10 to the recess 32.

The valve member shown 51, shown in FIGS. 4 and 5 may also be injection molded from plastic. The valve member 51 includes a substantially tubular holow housing 50 closed at one end by a wall 52. The valve member 51 has an arm 54 which extends radially outwardly therefrom. A flat handle 56 is formed as an integral part of the arm 54 and extends upwardly therefrom. The handle 56 serves as a deformable portion of the valve member 51. The handle 56 has a detent surface 58 positioned for engagement with a cooperating detent surface 60 on the rib 40 of the valve body 35. As illustrated in FIG. 5, one surface of the handle 56 bears the legend "closed" and the other (non-visible) surface bears the legend "open". A liquid exit port 62 is provided in the housing 50. The liquid exit port 62 registers with the liquid exit port 37 when the valve member 51 is in one rotational position relative to the valve body 35. The liquid exit port 62 is closed off by the valve body 35 when the valve member 51 is in the other rotational position relative to the valve body 35. In normal use, the handle 56 is moved between its two possible limit positions. At one limit position, the handle 56 is generally parallel to the flange 36 on one side of the central axis of the valve body 35. In the other position, the handle 56 is generally parallel to the flange 36 on the other side of the central axis of the valve body 35. When the ports 37, 62 are aligned the "open" legend is exposed, whereas when the handle 56 and arm 54 are positioned as shown in FIG. 5 the ports 37, 62 are not aligned, so the "closed" legend is exposed. The apparatus of the present invention is particularly convenient to use and is easy to operate, even by old and infirm people. In addition, the clear legend on the handle 56 avoids any confusion as to whether the tap 30 is closed or open.

If it is desired to separate the valve member 51 from the valve body 35, for cleaning, for example, then the handle 56 is deformed away from the housing 50 so that the detent surfaces 58, 60 are disengaged. When disengaged, the valve member 51 is readily withdrawn axially downwards.

A land 66 of short axial length is preferably provided on the external cylindrical surface of the valve member 51, in order to improve the retention of the valve member 51 in the valve body 35.

With reference now to FIGS. 1, 2, 6, and 7, the cylindrical wall 34 has a hole 80 formed therethrough. The hole 80 is covered by a pad 82 of air-permeable material. In the preferred embodiment of the invention, the material used is known commercially as Micropore. If desired, the air-permeable pad 82 may be impregnated with a bacteriacide or an odor removing substance.

The pad 82 is attached to the cylindrical wall 34 in any desired manner. In the preferred embodiment of the invention, an adhesive material is used to attach the pad 82 to the body 34.

Figure 6:
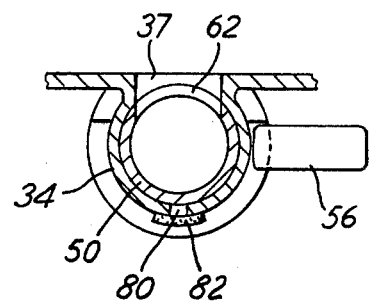
FIG. 6 is a horizontal cross-sectional view of the tap shown in FIG. 1 illustrating the valve member in the "open" position.
Figure 7:
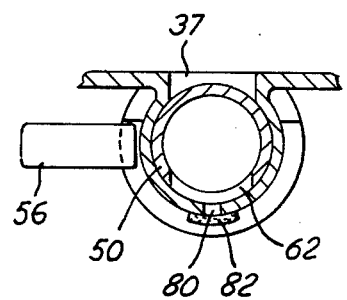
FIG. 7 is a horizontal cross-sectional view of the tap shown in FIG. 1 illustrating the valve member in the "closed" position, wherein an air entry path to the outlet tube is illustrated.

As shown in FIG. 7, the hole 80 is located so that it is aligned with the hole 62 when the handle 56 is in its closed position, and, as shown in FIG. 6, the hole 80 is shut off when the handle 56 is in its open position. When the tap is closed, air can enter the interior of the valve member 50, and can thereby enter the interior of a drainage tube extending down from the tap outlet. In this way, there is no build-up of negative pressure in the drainage tube, a condition known as "pooling". At the same time, no liquid can exit through the hole 80.

It will be seen that the invention as paticularly disclosed and illustrated herein provides a simple two-part tap which can readily be mass produced, which can readily be rapidly fixed to a drainage bag, and which is simple, easy, and relatively foolproof to operate.

I claim:

1. A tap which can be readily fixed in a face-to-face manner to a wall of a plastic drainage bag comprising:
    (a) a body with a substantially cylindrical recess formed therein, said body having a rib located on the exterior surface thereof and a port which opens into said cylindrical recess;
    (b) a substantially cylindrical valve member in the form of a substantially hollow tube open at one end and having a port through a side wall thereof, said valve member having a deformable handle positioned thereon, said valve member being held within said recess in said body by engagement of said deformable handle with said rib, whereby said valve member is insertable and rotatable in said cylindrical recess of said body;
    (c) a flange on said body, whereby said body may be secured to a wall of said drainage bag, said port in said body extending through said flange, whereby at one rotational position of said valve member relative to said body, said port in said valve member registers with said port in said body, thereby opening said valve and providing a flow passage from said flange, through said ports, and out said open end of said valve member.

2. The tap of claim 1 wherein said valve body includes an air-permeable vent opposite said similar port in said body, whereby when said valve is open said air-permeable vent is closed, and when said valve is closed, said air-permeable vent is open.

3. The tap of claim 2 wherein said air-permeable vent is a port which is covered by an air-permeable material.

4. The tap of claim 3 wherein said air-permeable material is impregnated with a bacteriacide.

5. The tap of claim 3 wherein said air-permeable material is impregnated with an odor removing material.

6. The tap of claim 1 wherein said handle portion of said valve member extends substantially radially therefrom.

7. The tap of claim 6 wherein said handle has a deformable detent engageable with a rib on said body, whereby when said detent on said handle engages said rib on said body, as in normal use, said valve member is held within said body, yet said valve member is not prevented from rotating relative to said body.

8. The tap of claim 7 wherein said handle is in the form of an arm having a flat blade projecting radially outwardly from said valve member.

9. The tap of claim 8 wherein said handle has one side marked [e.g., by color or other indicia] to indicate that the valve is "closed".

10. The tap of claim 8 wherein said handle has one side marked to indicate that the valve is "open".

11. The tap of claim 7 wherein said body is formed to be integral with said flange, said flange being made of plastic and being welded, in a face-to-face manner, to a wall of said bag.

12. The tap of claim 9 wherein said body is formed to be integral with said flange, said flange being made of plastic and being adhesively fixed, in a face-to-face manner, to a wall of said bag.

* * * * *